US00PP20382P2

(12) United States Plant Patent
Heffron

(10) Patent No.: US PP20,382 P2
(45) Date of Patent: Oct. 6, 2009

(54) ***IMPATIENS* PLANT NAMED 'BALCEBIBU'**

(50) Latin Name: *Impatiens hawkeri*
Varietal Denomination: Balcebibu

(75) Inventor: Leslie Heffron, Granite Falls, NC (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/221,010

(22) Filed: Jul. 30, 2008

(51) Int. Cl.
*A01H 5/00* (2006.01)

(52) U.S. Cl. ..... Plt./318.6

(58) Field of Classification Search ..... Plt./318.6
See application file for complete search history.

(56) References Cited

OTHER PUBLICATIONS

Canada Plant Breeders' Rights Application No. 08-6199 filed Feb. 28, 2008 http://www.inspection.gc.ca.

*Primary Examiner*—Annette H Para
(74) *Attorney, Agent, or Firm*—Audrey Charles

(57) ABSTRACT

A new and distinct cultivar of *Impatiens* plant named 'Balcebibu', characterized by its single-type, light lavender-colored flower, medium green-colored foliage-colored foliage, and moderately vigorous, compact, and mounded growth habit.

1 Drawing Sheet

Latin name of genus and species of plant claimed: *Impatiens hawkeri.*

Variety denomination: 'Balcebibu'.

BACKGROUND OF THE INVENTION

The present invention relates to a new and distinct cultivar of *Impatiens* plant botanically known as *Impatiens hawkeri* and hereinafter referred to by the cultivar name 'Balcebibu'.

The new cultivar originated in a controlled breeding program in Arroyo Grande, Calif. during December 2004. The objective of the breeding program was the development of *Impatiens* cultivars with numerous large flowers, excellent basal branching, and a compact, mounded growth habit.

The new *Impatiens* cultivar is the result of cross-pollination. The female (seed) parent of the new cultivar is the proprietary *Impatiens hawkeri* breeding selection designated 8210-1, not patented, characterized by its single-type white-colored flowers, medium green-colored foliage, and vigorous, upright growth habit. The male (pollen) parent of the new cultivar is the proprietary *Impatiens hawkeri* breeding selection designated 8302-1, not patented, characterized by its single-type lavender-colored flowers having a white "eye", dark green-colored foliage, and minimally vigorous, compact growth habit. The new cultivar was discovered and selected as a single flowering plant within the progeny of the above stated cross-pollination during May 2005 in a controlled environment at Arroyo Grande, Calif.

Asexual reproduction of the new cultivar by terminal stem cuttings since May 2005 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcebibu' as a new and distinct cultivar of *Impatiens* plant:

1. Single-type, light lavender-colored flowers;
2. Medium green-colored foliage; and
3. Moderately vigorous, compact, and mounded growth habit.

Plants of the new cultivar differ from plants of the female parent primarily in flower color and growth habit and from plants of the male parent primarily in flower color and growth vigor.

Of the many commercially available *Impatiens* cultivars, the most similar in comparison to the new cultivar is HARMONY Lavender, not patented. However, in side by side comparisons, plants of the new cultivar differ from plants of HARMONY Lavender in at least the following characteristics:

1. Plants of the new cultivar have a lighter foliage color than plants of HARMONY Lavender; and
2. Plants of the new cultivar have a flower color slightly different from plants of HARMONY Lavender.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcebibu'. The plants were grown in 4.5 inch pots for 9 weeks in a greenhouse at West Chicago, Ill.

DETAILED BOTANICAL DESCRIPTION

Figure 1:
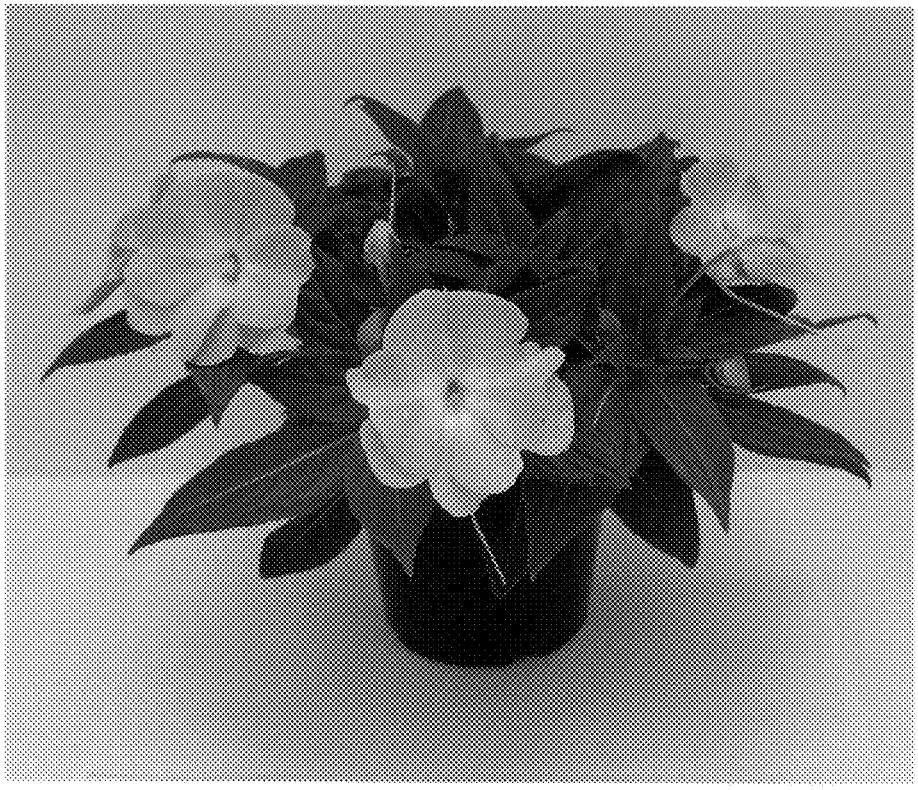
FIG. 1 illustrates a side view of the overall growth and flowering habit of 'Balcebibu'.
Figure 2:
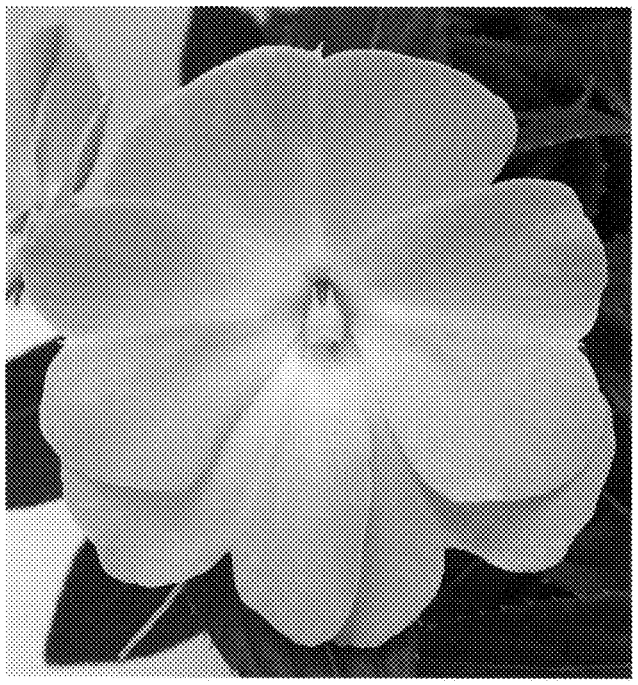
FIG. 2 illustrates a close-up view of an individual flower of 'Balcebibu'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jun. 24, 2008 between 9:00 a.m. and 11:00 a.m. under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Impatiens hawkeri* cultivar Balcebibu.

Parentage:

*Female parent.*—Proprietary *Impatiens hawkeri* breeding selection designated 8210-1, not patented.

*Male parent.*—Proprietary *Impatiens hawkeri* breeding selection designated 8302-1, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, compact, and mounded growth habit.

*Size.*—Height from soil level to top of plant plane: Approximately 14.0 cm. Width: Approximately 30.0 cm.

*Branching habit.*—Freely basal branching. Quantity of main branches per plant: Approximately 5.

*Branch.*—Strength: Strong. Length: Approximately 12.1 cm. Diameter at central internode: Approximately 6.0 mm. Length of central internode: Approximately 3.5 cm. Texture: Glabrous. Color of young and mature stems: 144B.

Foliage description:

*General description.*—Quantity of leaves per main branch: Approximately 10. Fragrance: None. Form: Simple. Arrangement: In whorls of 3 to 5 leaves.

*Leaves.*—Aspect: Petiole is at an acute angle to stem and leaf blade is perpendicular to stem. Shape: Elliptic. Margin: Serrate, ciliate. Apex: Acuminate. Base: Attenuate. Venation pattern: Pinnate. Length of mature leaf at center of stem: Approximately 9.4 cm. Width of mature leaf at center of stem: Approximately 3.7 cm. Texture of upper surface: Sparsely pubescent. Texture of lower surface: Sparsely pubescent on venation. Color of upper surface of young foliage: Closest to 137A with venation of 145C. Color of lower surface of young and mature foliage: Closest to 138A with venation of 145B. Color of upper surface of mature foliage: Closest to 139A with venation of 145C.

*Petiole.*—Length: Approximately 1.4 cm. Diameter: Approximately 3.0 mm. Texture: Glabrous. Color: 145C.

Flowering description:

*Flowering habit.*—'Balcebibu' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single. Quantity per plant: Approximately 5. Fragrance: None.

*Bud.*—Rate of opening: Generally takes 3 to 4 days for bud to progress from first color to fully open flower. Quantity showing color per plant: Approximately 2.

*Bud just before opening.*—Shape: Ovoid. Length: Approximately 1.9 cm. Diameter: Approximately 1.3 cm. Color: 75B.

*Corolla.*—Shape: Round, cupped when first open with petals turning downward with age. Width: Approximately 6.5 cm. Depth: Approximately 2.0 cm. Borne: Above and below foliage.

*Petals.*—Quantity: 5. Shape: Obovate. Aspect: Flat. Appearance: Iridescent. Margin: Entire. Apex: Emarginate. Base of upper petal: Truncate. Base of lateral and lower petals: Attenuate. Length of upper petal: Approximately 2.9 cm. Width of upper petal: Approximately 4.6 cm. Length of lateral petals: Approximately 3.1 cm. Width of lateral petals: Approximately 3.4 cm. Length of lower petals: Approximately 3.6 cm. Width of lower petals: Approximately 4.0 cm. Texture of upper and lower surfaces: Glabrous. Color of upper surface when first open: Between N80B and N80C with an eye of 155D. Color of lower surface when first and fully open: Lighter than N80D. Color of upper surface when fully open: Between N80C and N80D with an eye of 155D.

*Spur.*—Quantity: 1 per flower. Length: Approximately 6.5 cm. Diameter at proximal end: Approximately 2.0 mm. Diameter at distal end: Approximately 1.0 mm. Texture: Glabrous. Color: 145D with tip of 144A.

*Peduncle.*—Strength: Strong. Aspect: Acute angle to stem. Length: Approximately 6.8 cm. Diameter: Approximately 2.0 mm. Texture: Glabrous. Color: 145B.

*Sepals.*—Quantity per flower: 4 with one fused to base of upper petal. Shape of lateral sepals: Ovate. Shape of lower sepal: Ovate. Apex of all sepals: Acuminate. Length of lateral sepals: Approximately 1.4 cm. Width of lateral sepals: Approximately 6.0 mm. Length of lower sepal: Approximately 1.7 cm. Width of lower sepal: Approximately 1.5 cm. Texture of upper and lower surfaces of all sepals: Glabrous. Color of upper and lower surfaces of lateral sepals: 144B transitioning to 144A at tip. Color of upper and lower surfaces of lower sepal: Purer white than 155D with tip of 144B.

*Reproductive organs.*—Androecium: Stamen quantity: 5 per flower, fused around pistil at apex. Anther shape: Hooded. Anther length: Approximately 2.0 mm. Anther color: 158D. Filament color: 155D. Pollen amount: Abundant. Pollen color: 155D. Gynoecium: Pistil quantity: 1 per flower. Pistil length: Approximately 4.0 mm. Stigma shape: 5-pointed star. Stigma color: Colorless, transparent. Style color: 144A. Ovary texture: Glabrous. Ovary color: 144A.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balcebibu', substantially as herein shown and described.

* * * * *